United States Patent [19]

Sobotta et al.

[11] Patent Number: 5,565,037
[45] Date of Patent: Oct. 15, 1996

[54] PROCESS FOR PREPARING 1,2-5,6-DIACETONE-D-GLUCOSE

[75] Inventors: Rainer Sobotta, Ingelheim am Rhein; Franz D. Klingler, Griesheim, both of Germany

[73] Assignee: Boehringer Ingelheim GmbH, Ingelheim am Rhein, Germany

[21] Appl. No.: 267,099

[22] Filed: Jun. 24, 1994

[30] Foreign Application Priority Data

Feb. 10, 1993 [DE] Germany .......................... 43 03 821.2

[51] Int. Cl.$^6$ ............................... C07H 1/00; C07H 3/00
[52] U.S. Cl. ............................. 127/42; 127/58; 536/1.11; 536/124
[58] Field of Search ................... 536/1.11, 124; 127/42, 58

[56] References Cited

U.S. PATENT DOCUMENTS

| | | | |
|---|---|---|---|
| 4,551,523 | 11/1985 | Elam et al. ........................... | 536/119 |
| 5,256,800 | 10/1993 | Kaneko et al. ....................... | 549/174 |
| 5,399,201 | 3/1995 | Klingler et al. ..................... | 127/42 |

FOREIGN PATENT DOCUMENTS

| | | |
|---|---|---|
| 0076118 | 4/1983 | European Pat. Off. . |
| 0091223 | 10/1983 | European Pat. Off. . |
| 0139486 | 5/1985 | European Pat. Off. . |
| 0191464 | 8/1986 | European Pat. Off. . |

*Primary Examiner*—James J. Seidleck
*Assistant Examiner*—Duc Truong
*Attorney, Agent, or Firm*—Robert P. Raymond; Wendy E. Rieder; Alan R. Stempel

[57] ABSTRACT

The present invention relates to an improved process for preparing 1,2-5,6-diacetone-D-glucose from D-glucose and diketene or the adduct of diketene with acetone.

22 Claims, No Drawings

PROCESS FOR PREPARING 1,2-5,6-DIACETONE-D-GLUCOSE

The present invention relates to an improved process for preparing 1,2–5,6-diacetone-D-glucose (1,2:5,6-di-O-isopropylidene-α-glucofuranose)

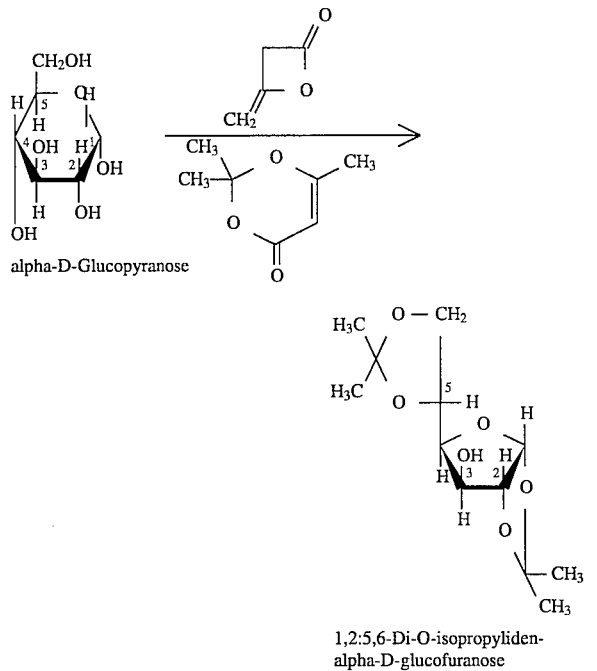

1,2:5,6-Di-O-isopropyliden-alpha-D-glucofuranose from D-glucose and diketene or the adduct of the diketene with acetone - which is entitled 2,2,6-trimethyl-1,3-dioxin-4-one.

1,2–5,6-Diacetone-D-glucose is a central intermediate product for numerous other glucose derivatives, some of which are of great importance as drugs. Examples include 2-deoxy-D-riboseanilide or amiprilose.

In addition, 1,2–5,6-diacetone-D-glucose can be used as a chiral ligand in complexes which permit enantioselective reactions [F. D. Klingler and M. Psiorz, Chimicaoggi 1992, 47].

This central role of 1,2–5,6-diacetone-D-glucose is responsible for the fact that the annual requirement of this intermediate product is measured in tonnes.

It is generally known from the prior art that monosaccharides which contain two sterically adjacent OH groups in the cis-position can be reacted with aldehydes or ketones in the presence of sulphuric acid, zinc chloride or phosphorus(V)-oxide to obtain the corresponding acetals (E. Fischer, 1895).

Thus, 1,2:5,6-di-O-isopropylidene-α-D-glucofuranose (diacetone-α-D-glucose) can be obtained by reacting D-glucosa with acetone in the presence of sulphuric acid. In order to achieve high conversions, the water resulting from the ketalisation must be bound or eliminated from the reaction mixture.

Moreover, the preparation of diacetone glucose in the presence of acidically reacting catalysts such as Lewis acids, e.g. complex compounds of boron trifluoride, aluminium halides—such as aluminium(III)-chloride or —bromide—, tin salts or halides of rare earths is known from the prior art.

Other catalysts known from the prior art include iodine, gypsum or molecular sieves. However, the use of catalysts which have hitherto been regarded as suitable—not only in terms of reactions on an industrial scale—has serious disadvantages, of which the following are mentioned by way of example:

when inorganic acids or phosphorus pentoxide are used large quantities of these agents are required, which on the one hand results in only a low throughput and on the other hand incurs major problems of disposal of the salts resulting from the neutralisation which has to be carried out afterwards;

when iodine is used, large quantities of solvent are required which again permit only a small throughput;

when an additional solvent is used which is capable of forming an azeotrope with water, a further increase in the volume of the reactor vessel is essential, and moreover the use of an entraining agent such as pentane, for example, involves a lowering of the boiling point, thus limiting the reaction temperature and correspondingly lengthening the reaction time;

the use of solid catalysts also presents problems as a result of the reactions of caramelisation which also take place and moreover the recovery of ion exchangers, for example, involves a great deal of expense;

in addition, many reactions have the disadvantage that the secondary reactions—which are dependent in their extent on the particular reaction conditions—such as the self-condensation of acetone—produce, in some cases, tarry by-products which on the one hand affect the effectiveness of the catalyst and on the other hand lead to an undesirable contamination of the reaction product which in some cases can only be removed by chromatographic purification.

The objective of the present invention is therefore to overcome the disadvantages of the methods of preparing diacetone glucose known from the prior art.

According to the invention this objective is achieved by reacting D-glucose with diketene or with the diketene-acetone adduct (2,2,6-trimethyl-1,3-dioxin-4-one)—which can be used as diketene equivalent—in acetone. The use of diketene or the diketene-acetone adduct in the preparation of 1,2–5,6-diacetone-D-glucose (1,2:5,6-di-O-isopropylidene-α-D-glucofuranose) has the advantage that this reaction does not produce any waste products which have to be disposed of, in some cases with difficulty. Moreover, the process according to the invention uses a relatively small volume of acetone as solvent.

In order to carry out the process according to the invention the (anhydrous) D-glucose and the diketene or the 2,2,6-trimethyl-1,3-dioxin-4-one is dissolved in acetone and mixed with a catalytic amount of Lewis acid or a Brönsted acid. Examples of Lewis acids used in the process according to the invention include halides of boron, preferably complex boron halides and, particularly preferably, the boron trifluoride-etherate complex. Examples of Brönsted acids which may be used are inorganic acids (such as sulphuric acid) or organic acids (such as toluenesulphonic acid).

The reaction mixture is then heated to a temperature in the range from 60° to 120° C., preferably 80° to 100° C. and, particularly preferably, to 90° C. After the end of the reaction, the reaction mixture is cooled and filtered. In the subsequent reaction step the filtrate thus obtained is mixed with the aqueous solution of an alkaline-reacting compound, preferably with the aqueous solution of an alkaline or alkaline earth metal hydroxide and more especially with dilute sodium hydroxide solution until the reaction mixture has achieved a pH in the range from 6 to 8, preferably 6.5 to 7.5 and most preferably has reached a pH of about 7. Then the acetone is largely distilled off in vacuo and the residue is subsequently extracted with a water-immiscible extraction agent. Examples of suitable extraction agents for this purpose include aliphatic or aromatic hydrocarbons, preferably halogenated hydrocarbons, cycloalkanes or alkyl aromatics, of which dichloromethane, cyclohexane and toluene are particularly preferred. The combined extracts are evaporated down in vacuo, optionally after being dried, and the residue remaining is recrystallised from a suitable organic solvent. Alkanes such as petroleum fractions and especially cycloalkanes such as cyclohexane are suitable for this purpose. The crystals thus obtained are then isolated and dried.

The objectives set out hereinbefore are achieved by means of the processes described in the Examples. A variety of other embodiments of the process will become apparent from this specification to those skilled in the art. However, it should be expressly pointed out that the Examples and the associated specification are provided merely for the purpose of explanation and description and should not be regarded as a limitation of the invention. In particular, it is pointed out that the synthesis sequence described in the Examples for preparing 1,2:5,6-di-O-isopropylidene-α-D-glucofuranose can also be applied to the preparation of other isopropylidene sugars.

The following monosaccharides are mentioned as examples of possible starting materials:

D-galactose, L- and D-arabinose, fructose, sorbose, D-xylose, D-mannose, D-ribose, D-mannitol or L-ascorbic acid.

EXAMPLE 1

Reaction of D-glucose with diketene 54.1 g (300 mmol) of anhydrous α-D-(+)-glucose and 26.5 g (300 mmol) of diketene (3-hydroxy-3-butenoic acid-lactone) are dissolved in 1.1 liters of acetone and mixed with 0.85 g (5.2 mmol) of boron trifluoride-diethylether complex and heated to 90° C. over a period of about 4.5 hours in a stirred autoclave with stirring. After cooling to ambient temperature the reaction solution is filtered and mixed with 350 ml of 1% sodium hydroxide solution. Then the acetone is distilled off in vacuo. The residue remaining is extracted three times with dichloromethane. The combined extracts are evaporated down in vacuo and the residue remaining is recrystallised from cyclohexane. The 1,2–5,6-diacetone-D-glucose (1,2:5,6-di-O-isopropylidene-α-D-glucofuranose) is obtained in the form of a colourless crystalline solid in a yield of 63% of theory.

EXAMPLE 2

Reaction of D-glucose with the diketene-acetone adduct 54.1 g (300 mmol) of anhydrous α-D-(+)-glucose and 50.2 g (300 mmol) of diketene-acetone adduct (2,2,6-trimethyl-1,3-dioxin-4-one) (85% strength) are dissolved in 1.1 liters of acetone and mixed with 0.85 g (5.2 mmol) of boron trifluoride-diethylether complex and heated in a stirred autoclave for a period of about 4.5 hours to 90° C. with stirring. After cooling to ambient temperature the reaction solution is filtered and mixed with 350 ml of 1% sodium hydroxide solution.

Then the acetone is distilled off in vacuo. The residue remaining is extracted three times with dichloromethane. The combined extracts are evaporated down in vacuo and the residue remaining is recrystallised from cyclohexane. The 1,2–5,6-diacetone-D-glucose (1,2:5,6-di-0-isopropylidene-α-D-glucofuranose) is obtained in the form of a colourless crystalline solid in a yield of 58% of theory.

What is claimed is:

1. A process for preparing 1,2–5,6-diacetone-D-glucose, comprising the step of reacting a α-D-glucose with diketene in the presence of a Lewis acid or a Brönsted acid in acetone.

2. A process for preparing 1,2–5,6-diacetone-D-glucose comprising the step of reacting α-D-glucose with 2,2,6-trimethyl-1,3-dioxin-4-one in the presence of a Lewis acid or a Brönsted acid in acetone.

3. The process according to claim 1 or 2, wherein the reaction mixture is heated to a temperature in the range from 60° to 120° C.

4. The process according to claim 3, wherein the reaction mixture is heated in the temperature range from 80° to 100° C.

5. The process according to claim 1 or 2 wherein the Lewis acid is a complex boron halide.

6. The process according to claim 5, wherein the complex boron halide is a boron trifluoride etherate complex.

7. The process according to claim 1 or 2 wherein the Brönsted acid is an inorganic acid.

8. The process according to claim 7, wherein the inorganic acid is sulfuric acid.

9. The process according to claim 1 or 2 wherein the Brönsted acid is an organic acid.

10. The process according to claim 9, wherein the organic acid is toluenesulphonic acid.

11. The process according to claim 1 or 2 further comprising the step of cooling and filtering the reaction mixture to yield a filtrate, then reacting the filtrate with an aqueous solution of an alkaline-reacting compound until the filtrate has achieved a pH in the range from 6 to 8.

12. The process according to claim 11 wherein the alkaline-reacting compound is an alkaline or alkaline earth metal hydroxide.

13. The process according to claim 12, wherein the alkaline or alkaline earth metal hydroxide is sodium hydroxide.

14. The process according to claim 11, further comprising the steps of removing the acetone, then extracting the residue with a water-immiscible extraction agent.

15. The process according to claim 14, wherein the water-immiscible extraction agent is selected from the group consisting of aliphatic and aromatic hydrocarbons, cycloalkanes and alkyl aromatics.

16. The process according to claim 15, wherein the water-immiscible extraction agent is dichloromethane, cyclohexane or toluene.

17. The process according to claim 14, further comprising the step of recrystallising the residue from a suitable organic solvent.

18. The process according to claim 17, wherein the organic solvent is an alkane cr a cycloalkane.

19. The process according to claim 18, wherein the organic solvent is a petroleum fraction or cyclohexane.

20. A process for preparing 1,2–5,6-diacetone-D-glucose, comprising the steps of:

(a) reacting α-D-glucose with diketene or 2,2,6-trimethyl-1,3-dioxin-4-one, in the presence of a Lewis acid or a Brönsted acid in acetone at a temperature in the range from 60° to 120° C.;

(b) cooling the mixture;

(c) freeing the mixture from step (b) from any solid constituents;

(d) combining the mixture from step (c) with an aqueous solution of an alkaline-reacting compound, until a pH in the range from 6 to 8 is achieved;

(e) distilling off the acetone to yield a residue;

(f) extracting the residue with a water-immiscible organic extraction agent;

(g) evaporating the combined extracts from step (f) and (h) recrystallising the product from step (g) from an organic solvent; and (i) isolating the 1,2–5,6-diacetone-D-glucose product.

21. The process according to claim 20, wherein the Lewis acid or Brönsted acid in step (a) comprises boron halides, complex boron halides, an inorganic acid or an organic acid: step (a) is conducted at a temperature in the range from 80° to 100° C.; the aqueous solution of an alkaline-reacting compound in step (d) is an alkaline or alkaline earth metal hydroxide; the pH in step (d) is in the range from 6.5 to 7.5; the water-immiscible organic extraction agent in step (f) is a halogenated hydrocarbon, a cycloalkane or an alkyl aromatic; and the organic solvent in step (h) is an alkane or a cycloalkane.

22. The process according to claim 21, wherein the Lewis acid or Brönsted acid in step (a) is boron trifluoride diethylether complex; step (a) is conducted at a temperature of 90°; the aqueous solution of an alkaline-reacting compound in step (d) is a dilute sodium hydroxide solution; the pH in step (d) is 7; the water-immiscible organic extraction agent in step (f) is dichloromethane; and the organic solvent in step (h) is cyclohexane.

* * * * *